United States Patent [19]
Messina

[11] Patent Number: 5,183,661
[45] Date of Patent: * Feb. 2, 1993

[54] DEER REPELLENT DEVICE AND METHOD

[76] Inventor: James Messina, Rte. 24, Box 122, Chester, N.J. 07930

[*] Notice: The portion of the term of this patent subsequent to Oct. 23, 2007 has been disclaimed.

[21] Appl. No.: 804,776

[22] Filed: Dec. 9, 1991

[51] Int. Cl.⁵ .................. A01N 25/24; A01N 65/00; A01N 47/14
[52] U.S. Cl. .................................... 424/405; 514/920; 514/479; 428/907; 424/195.1
[58] Field of Search ...................... 424/405; 514/920; 428/907

[56] References Cited

U.S. PATENT DOCUMENTS

| | | | |
|---|---|---|---|
| 4,657,759 | 4/1987 | Hansen et al. | 424/83 |
| 4,666,767 | 5/1987 | von Kohorn et al. | 428/304.4 |
| 4,735,803 | 4/1988 | Katz et al. | 424/195.1 |
| 4,965,070 | 10/1990 | Messina | 424/581 |

Primary Examiner—Thurman K. Page
Assistant Examiner—Neil Levy
Attorney, Agent, or Firm—Ribis Graham & Curtin

[57] ABSTRACT

A deer repellent device and method for warding off a deer from a shrub or plant. The device is an assembly of a deer repellent formulation and a support medium for the formulation. The support medium is a length of rope or a volume of clay granules, the rope, as treated, can be strung around shrubs or along plants. The clay medium, as treated, can be placed under and around a shrub or plant.

4 Claims, No Drawings

DEER REPELLENT DEVICE AND METHOD

The invention generally relates to a deer repellent device, and in particular the invention relates to a deer repellent device having a deer repellent formulation with a support medium.

BACKGROUND OF THE INVENTION

The prior art deer repellent formulation is described in U.S. Pat. No. 4,965,070, issued Oct. 23, 1990 to the same inventor as this application.

The prior art formulation consisted essentially of by volume:
- 84% water;
- 8% thiram;
- 1% chicken eggs;
- 1% liquid hot sauce;
- 5% adhesive.

One problem of the prior art deer repellent formulation is the difficulty of maintaining such formulation on a shrub, or plant, or the like, during snow or rain.

OBJECTS OF THE INVENTION

One object of the present invention is to support a deer repellent formulation on a shrub, or plant, or the like, during exposure to snow or rain.

Another object is to support a deer repellent formulation adjacent to a relatively low plant or the like.

Still another object is to support a deer repellent formulation spaced away from a shrub, or plant, or the like.

SUMMARY OF THE INVENTION

According to the present invention, a deer repellent device and method are provided. This device comprises a deer repellent formulation, and a support medium on which the formulation is supported. The method of making the deer repellent device includes the steps of making a deer repellent formulation, and then supporting the deer repellent formulation evenly along or through the support medium. In a first embodiment, the support medium is a length of sash cord. In a second embodiment, the support medium is a volume of clay material having a selective particle size distribution.

DESCRIPTION OF THE PREFERRED EMBODIMENT

In the first embodiment of the invention, the support medium is a solid braid, number 8, cotton and polyester, one-quarter inch diameter, sash cord rope of 100 foot length, which is sold by the Lehigh Group, Allentown, Pennsylvania 18105, United States.

In the second embodiment of the invention, the support medium is a clay material, which ranges in size of clay granules or particles, from dustless fine granules to about one-quarter inch overall diameter or thickness granules. The clay material comes packaged in a 0.20 pound bag, which is made of a finely woven cloth material and which has a drawstring along an open top edge thereof, and which has a size of about 4 inches in height by about 3 inches in width when flat. The drawstring threads through spaced holes located about one-half inch down from the bag top edge.

The deer repellent formulation is described in detail in the above-mentioned U.S. Pat. No. 4,965,070.

Thiram is the coined common name for the chemical tetramethylthiram with the formula $C_6H_{12}N_2S_4$ is commonly used as a fungicide and as a seed disinfectant. Thiram is packaged in 75 percent concentration dry.

Thiram is mixed with water to produce a water solution. A selective weight of chicken eggs, which are deshelled or from their shells, are added to the solution. The eggs act as a deterrent agent. Pepper of a conventional type and of a selective weight is added to the solution. Pepper is used because inhalation of a pepper particle by an animal when sniffing a shrub, or low plant, causes momentary irritation of the respiratory system of the animal. This causes the animal to retreat from the shrub, or low plant. A coloring dye is an optional addition to the solution for blending the deer repellent assembly with the landscape. A coloring dye, such as that sold in under the names, Greenzit, can be used. An adhesive, such as that sold under the trademark "Nu-Film-P", or the like, can be used. In particular, the adhesive is used for a deer repellent assembly, which is exposed to rain or snow.

The deer repellent assembly of support rope and formulation can be wrapped around a shrub or plant or strung between shrubs and plants. The deer repellent assembly of support medium clay material and formulation can be distributed under and around shrubs and plants, or the like.

It is noted that 16 fluid ounces of deer repellent formulation is sufficient to wet the 100 foot length of one-quarter inch diameter rope. Also, eleven fluid ounces of deer repellent formulation is sufficient to wet throughout the one pound of clay granules. A shorter rope length requires proportionally less fluid ounces of formulation based upon rope length and rope cross section areas. Less than one pound of clay granules medium requires proportionally less fluid ounces of formulation based upon medium volume.

EXAMPLE I

The deer repellent assembly in the first embodiment is shown below:

a 100 foot length of support rope of one-quarter inch diameter, and of cotton and polyester, solid braid material;

16 fluid ounces of deer repellent formulation, consisting of about 15 fluid ounces of water and about 0.125 ounces by weight of deshelled chicken eggs and about 0.063 ounces by weight of pepper and about 0.968 ounces by weight of seventy-five percent thiram dry and an adhesive in a quantity sufficient for adherence to the support rope and a coloring dye in an amount sufficient to produce a desired color;

said deer repellent formulation being about evenly distributed along the support rope length.

EXAMPLE II

The deer repellent assembly in the second embodiment is shown below:

one pound by weight of clay granules in a particle size distribution from dustless fine particles to about one-quarter inch overall thickness particles for a support medium;

eleven fluid ounces of deer repellent formulation consisting of about ten fluid ounces of water and about 0.086 ounces by weight of deshelled chicken eggs and about 0.044 ounces by weight of pepper and about 0.665 ounces by weight of seventy-five percent thiram dry and an adhesive in a quantity sufficient for adherence to the support medium clay granules and a coloring dye in an amount sufficient to produce a desired color;

said deer repellent formulation being about evenly distributed throughout the support medium clay granules.

What is claimed is:

1. A deer repellent assembly comprising:
   a 100 foot length of one-quarter inch diameter elongate flexible rope of a cotton and polyester solid braid material for use as a support medium;
   16 fluid ounces of deer repellent liquid formulation consisting of about 15 fluid ounces of water and about 0.125 ounces by weight of deshelled chicken eggs and about 0.063 ounces by weight of pepper and about 0.968 ounces by weight of seventy-five percent thiram dry and an adhesive in a quantity sufficient for adherence to the flexible rope; and
   said deer repellent liquid formulation being evenly distributed along the entire length of the flexible rope sufficient to wet the rope.

2. A deer repellent assembly comprising:
   a selected length of elongate flexible rope of a selected size diameter of a cotton and polyester solid braid material for use as a support medium;
   a selected volume of deer repellent liquid formulation based upon about 16 fluid ounces of formulation per 0.20 square inch section area and per 100 foot length of support rope, said 16 fluid ounces of formulation prior to water evaporation consisting of about 15 fluid ounces of water and about 0.125 ounces of weight of deshelled chicken eggs and about 0.063 ounces by weight of pepper and about 0.968 ounces by weight of seventy-five percent thiram dry and an adhesive in a quantity sufficient for adherence to the flexible rope; and
   said formulation being about evenly distributed along the entire length of the flexible rope and sufficient to wet the rope.

3. A method of repelling deer from shrubs, including the steps of:
   preparing a deer repellent liquid formulation as described in claim 3;
   forming an elongate flexible rope as described in claim 3 for use as a support medium for the formulation;
   distributing the liquid formulation evenly on the entire rope sufficient to wet the rope; and
   disposing portions of the rope on and about the shrubs.

4. The method as defined in claim 3, wherein the rope is a braided rope of about one-quarter inch diameter.

* * * * *